(12) United States Patent
Miquel

(10) Patent No.: US 11,166,840 B2
(45) Date of Patent: *Nov. 9, 2021

(54) MANDIBULAR PROTRUSION DEVICE

(71) Applicant: Panthera Dental Inc., Quebec (CA)

(72) Inventor: Florent Miquel, Quebec (CA)

(73) Assignee: Panthera Dental Inc., Quebec (CA)

( * ) Notice: Subject to any disclaimer, the term of this patent is extended or adjusted under 35 U.S.C. 154(b) by 55 days.

This patent is subject to a terminal disclaimer.

(21) Appl. No.: 16/509,538

(22) Filed: Jul. 12, 2019

(65) Prior Publication Data

US 2019/0336323 A1 Nov. 7, 2019

Related U.S. Application Data

(63) Continuation of application No. 14/430,568, filed as application No. PCT/CA2013/050726 on Sep. 24, 2013, now Pat. No. 10,390,990.

(30) Foreign Application Priority Data

Sep. 24, 2012 (CA) .................................. CA 2791139

(51) Int. Cl.
*A61F 5/00* (2006.01)
*A61F 5/56* (2006.01)
(Continued)

(52) U.S. Cl.
CPC ................ *A61F 5/566* (2013.01); *A61C 7/36* (2013.01); *A61C 11/001* (2013.01)

(58) Field of Classification Search
CPC ........... A61C 7/08; A61C 7/36; A63B 71/085; A61F 5/37; A61F 5/56; A61F 5/566
(Continued)

(56) References Cited

U.S. PATENT DOCUMENTS 3,080,634 A 3/1963 Lindblad
4,424,032 A 1/1984 Howe
(Continued)

FOREIGN PATENT DOCUMENTS

CH 682883 A5 12/1993
CN 2418850 Y 2/2001
(Continued)

OTHER PUBLICATIONS

Bloch et al. "A Randomized, Controlled Crossover Trial of Two Oral Appliances for Sleep Apnea Treatment", American Journal of Respiratory and Critical Care Medicine, vol. 162., 2000, pp. 246-251.
(Continued)

*Primary Examiner* — Keri J Nelson
*Assistant Examiner* — Adam Baker
(74) *Attorney, Agent, or Firm* — Marshall, Gerstein & Borun LLP

(57) ABSTRACT

A mandibular protrusion device which comprises a maxillary dental tray, a mandibular dental tray and at least two lateral links. Each one of the lateral links has a first end removably engageable with the maxillary dental tray and a second end removably engageable with the mandibular dental tray. The maxillary dental tray, mandibular dental tray and the lateral links have complementary male and female members configured to be engageable and disengageable from one another in at least one engagement/disengagement configuration that is not reached when the device is worn or in normal use.

24 Claims, 15 Drawing Sheets

(51) Int. Cl.
*A61C 7/36* (2006.01)
*A61C 11/00* (2006.01)

(58) Field of Classification Search
USPC .... 433/5–8, 19, 24, 140; 128/848, 859, 861, 128/862
See application file for complete search history.

(56) References Cited

U.S. PATENT DOCUMENTS

| | | |
|---|---|---|
| 4,551,095 A | 11/1985 | Mason |
| 5,011,404 A | 4/1991 | Losi |
| 5,678,990 A | 10/1997 | Rosenberg |
| 5,879,157 A | 3/1999 | Scheu |
| 5,897,313 A | 4/1999 | Cleary et al. |
| 5,947,724 A | 9/1999 | Frantz et al. |
| 6,012,920 A | 1/2000 | Woo |
| 6,055,986 A | 5/2000 | Meade |
| 6,109,265 A | 8/2000 | Frantz et al. |
| 6,234,792 B1 | 5/2001 | DeVincenzo |
| 6,302,686 B1 | 10/2001 | Chott et al. |
| 6,418,933 B1 | 7/2002 | Strong |
| 7,146,982 B2 | 12/2006 | Mousselon et al. |
| 7,810,502 B1 | 10/2010 | Nguyen et al. |
| 7,987,854 B2 | 8/2011 | Arni |
| 2001/0036615 A1 | 11/2001 | Binder |
| 2007/0224567 A1 | 9/2007 | Robson |
| 2011/0259345 A1 | 10/2011 | Cullen |
| 2012/0073582 A1 | 3/2012 | Kopp |
| 2013/0140289 A1 | 6/2013 | Baratier et al. |

FOREIGN PATENT DOCUMENTS

| | | |
|---|---|---|
| DE | 295 06 512 U1 | 6/1995 |
| DE | 197 46 157 C2 | 5/1998 |
| DE | 201 02 432 U1 | 4/2001 |
| EP | 0 794 749 B1 | 6/2003 |
| EP | 1 459 699 A1 | 9/2004 |
| EP | 1 516 604 A1 | 3/2005 |
| EP | 2 143 397 A1 | 1/2010 |
| WO | WO-02/38090 A1 | 5/2002 |
| WO | WO-03/034957 A2 | 5/2003 |

OTHER PUBLICATIONS

Dischinger. "Edgewise Herbst Appliance", JCO, Inc., vol. 29, No. 12, 1995, pp. 738-742.
Langenhan et al., "Intraorale Protrusionsschienen bei OSAS und Schnarchen—Aktualisierte zahnmedizinische und zahntechnische Standards", Quintessenz Zahntech, vol. 36, No. 6, 2010, pp. 774-790.
Langenhan et al. "Beitrage aus der Quintessenz und der Quintessenz Zahntechnik", Quintessenz, Focus Zahnmedizin, Schlafapnoe, 2010, pp. 1-16.
Petelle et al., "One-Night Mandibular Advancement Titration for Obstructive Sleep Apnea Syndrome—A Pilot Study", American Journal of Respiratory and critical care medicine, vol. 165, 2002, pp. 1150-1153.
Randerath et al., "An Individually Adjustable Oral Appliance vs Continuous Positive Airway Pressure in Mild-to—Moderate Obstructive Sleep Apnea Syndrome", Chest Journal, vol. 122, vol. 2, 2002, pp. 569-575.
Rogers, "Troubleshooting the Herbst Appliance", JCO, INC., vol. XXXVI, No. 5, May 2002, pp. 268-274.
Rose, "Die Wertigkeit oraler Therapie-verfahren zur Behandlung des Schnarchens und der obstruktiven Schlafapnoe", Scheweiz Monatsschr Zahnmed. vol. 112. No. 4, 2001, pp. 359-365.
Sanner et al., "Oral Appliances for the treatment of Obstructive Sleep Apnea", Somnologie, vol. 3, 1999, pp. 62-66.
Taugerbeck, "Comparison of Dental Intraloral Devices for Snoring Therapy : A Subjective Survey of their Effect on Mixed Sleep Apnea Syndrome", Patients and Doctors Forum, 1997, pp. 20-31.
International Search Report and Written Opinion in International Application No. PCT/CA2013/050726 dated Jan. 2, 2014, 8 pages.
International Preliminary Report on Patentability in International Application No. PCT/CA2013/050726 dated Feb. 2, 2015, 22 pages.

MANDIBULAR PROTRUSION DEVICE

CROSS REFERENCE TO RELATED APPLICATION

This application is a continuation of U.S. application Ser. No. 14/430,568, which is the U.S. national phase of PCT/CA2013/050726 filed Sep. 24, 2013, which claims the benefit under 35 U.S.C. § 119 of Canadian patent application Serial No. 2,791,139, filed Sep. 24, 2012, the entire respective disclosures of which are incorporated herein by reference.

TECHNICAL FIELD OF THE INVENTION

The technical field relates to mandibular protrusion devices. More particularly, it relates to a mandibular protrusion device having a maxillary dental tray connected to a mandibular dental tray by lateral links providing an articulation therebetween.

BACKGROUND

It is known in the art to use dental appliances for the treatment of snoring and sleep apnea. For example and without being limitative, the dental appliances can be intraoral orthoses which prevent the mandible from moving posteriorly during sleep.

One type of known intraoral orthosis includes two dental trays (or bite forms) joined together so that the user's mandible projects forwardly from its normal position and thereby helps reducing snoring and sleep apnea. In such an orthosis, the dental trays are connected to one another through two lateral links which are configured to advance the user's mandible during a vertical movement between the maxilla and the mandible. In some embodiments, for connection to the dental trays corresponding to the maxilla or the mandible, the lateral links have a protrusion inserted in a through hole of the dental trays.

One of the common drawbacks of known intraoral orthoses is that the lateral links often disconnect from the dental tray to which they are engaged, when the intraoral orthosis is being manipulated. In such cases, the user must spend time to reconnect the disconnected lateral link to its respective dental tray.

In view of the above, there is a need for an improved mandibular protrusion device which, by virtue of its design and components, would be able to overcome or at least minimize some of the above-discussed prior art concerns.

BRIEF SUMMARY OF THE INVENTION

According to a first general aspect, there is provided a mandibular protrusion device which comprises a maxillary dental tray, a mandibular dental tray and at least two lateral links. Each one of the lateral links has a first end removably engageable with the maxillary dental tray and a second end removably engageable with the mandibular dental tray. The maxillary dental tray, mandibular dental tray and the lateral links have complementary male and female members configured to be engageable and disengageable from one another in at least one engagement/disengagement configuration that is not reached when the device is worn or in normal use.

In an embodiment, the engagement/disengagement configuration is a single configuration for each one of the at least two lateral links.

In an embodiment, each one of the complementary male and female members of the maxillary dental tray, mandibular dental tray and the at least two lateral links has a particular predetermined shape. The engagement/disengagement configuration is reached when the predetermined shape of the corresponding ones of the male and female members of the maxillary dental tray, mandibular dental tray and the at least two lateral links are aligned.

In an embodiment, the at least two lateral links include a right side lateral link and a left side lateral link. The engagement/disengagement configuration is different for the right side lateral link and the left side lateral link.

In an embodiment, the engagement/disengagement configuration of one of the right side lateral link and the left side lateral link is at about 200° and the engagement/disengagement configuration of the other one of the right side lateral link and the left side lateral link is at about 170° with respect to a configuration where the maxillary dental tray and the mandibular dental tray are superposed.

In an embodiment, the complementary male and female members of the maxillary dental tray, mandibular dental tray and the at least two lateral links are substantially L-shaped.

In an embodiment, each one of the male members includes a pivot portion rotatable into a corresponding complementary female member and connected to a substantially L-shaped enlarged head.

In an embodiment, the at least two lateral links include the male members and the maxillary dental tray and mandibular dental tray include the complementary female members.

In an embodiment, a first one of the male members protrude on a first side of the lateral links and a second one of the male members protrude on a second side of the lateral links.

In an embodiment, each one of the at least two lateral links is engageable with the mandibular dental tray by engaging the mandibular dental tray from an inner side towards an outer side of the mandibular dental tray and each one of the at least two lateral links is engageable with the maxillary dental tray by engaging the maxillary dental tray from an outer side towards an inner side of the maxillary dental tray.

In an embodiment, each one of the at least two lateral links has an elongated portion extending between the first end and the second end, the elongated portion having a curvature defined therein.

In an embodiment, each one of the at least two lateral links is thicker along sections of the elongated portion and towards the first end and the second end.

In an embodiment, each one of the at least two lateral links is narrower in a central section of the elongated portion than close to the first end and the second end.

In an embodiment, the mandibular dental tray is configured for engagement between the complementary male and female members of the at least two lateral links and the mandibular dental tray to occur above a contact plan between sections of the maxillary dental tray and the mandibular dental tray.

In an embodiment, the mandibular dental tray is configured for engagement between the complementary male and female members of the at least two lateral links and the mandibular dental tray to occur above an upper section of a wall of the mandibular dental tray.

In an embodiment, the lateral links are engageable with the mandibular dental tray in posterior sections thereof and forwardly thereof with the maxillary dental tray.

According to another general aspect, there is also provided a mandibular protrusion device comprising a maxillary dental tray, a mandibular dental tray and at least two lateral links removably engageable to the maxillary dental tray and the mandibular dental tray. The mandibular protrusion device is configurable between a plurality of operative configurations reached when the device is worn or in normal use and a non-operative configuration distinct from the plurality of operative configurations. The at least two lateral links are engageable and disengageable from the maxillary dental tray and the mandibular dental tray only when the mandibular protrusion device is configured in the non-operative configuration.

In an embodiment, the non-operative configuration ranges between 90° and 270° with respect to a configuration where the maxillary dental tray and the mandibular dental tray are superposed.

In an embodiment, the non-operative configuration comprises a single engagement/disengagement configuration for each one of the at least two lateral links. Each one of the at least two lateral links is engageable and disengageable from the maxillary dental tray and the mandibular dental tray only in its engagement/disengagement configuration.

In an embodiment, the at least two lateral links, the maxillary dental tray and mandibular dental tray include removably engageable complementary male and female members having a particular predetermined shape, the engagement/disengagement configuration being reached when the predetermined shape of the corresponding ones of the male and female members of the maxillary dental tray, mandibular dental tray and the at least two lateral links are aligned.

In an embodiment, the complementary male and female members of the maxillary dental tray, mandibular dental tray and the at least two lateral links are substantially L-shaped.

In an embodiment, each one of the male members includes a pivot portion rotatable into a corresponding complementary female member and connected to a substantially L-shaped enlarged head.

In an embodiment, the at least two lateral links include the male members and the maxillary dental tray and mandibular dental tray include the complementary female members.

In an embodiment, a first one of the male members protrude on a first side of the lateral links and a second one of the male members protrude on a second side of the lateral links.

In an embodiment, the at least two lateral links include a right side lateral link and a left side lateral link. The engagement/disengagement configuration is different for the right side lateral link and the left side lateral link.

In an embodiment, the engagement/disengagement configuration of one of the right side lateral link and the left side lateral link is at about 200° and the engagement/disengagement configuration of the other one of the right side lateral link and the left side lateral link is at about 170° with respect to a configuration wherein the maxillary dental tray and the mandibular dental tray are superposed.

In an embodiment, each one of the at least two lateral links is engageable with the mandibular dental tray by engaging the mandibular dental tray from an inner side towards an outer side of the mandibular dental tray and each one of the at least two lateral links is engageable with the maxillary dental tray by engaging the maxillary dental tray from an outer side towards an inner side of the maxillary dental tray.

In an embodiment, each one of the at least two lateral links has an elongated portion extending between a first end and a second end, the elongated portion having a curvature defined therein.

In an embodiment, each one of the at least two lateral links is thicker along sections of the elongated portion and towards the first end and the second end.

In an embodiment, each one of the at least two lateral links is narrower in a central section of the elongated portion than close to the first end and the second end.

In an embodiment, the mandibular dental tray is configured for the engagement between the at least two lateral links and the mandibular dental tray to occur above a contact plan between sections of the maxillary dental tray and the mandibular dental tray.

In an embodiment, the mandibular dental tray is configured for the engagement between the at least two lateral links and the mandibular dental tray to occur above an upper section of a wall of the mandibular dental tray.

In an embodiment, the lateral links are engageable with the mandibular dental tray in posterior sections thereof and forwardly thereof with the maxillary dental tray.

BRIEF DESCRIPTION OF THE DRAWINGS

Other objects, advantages and features will become more apparent upon reading the following non-restrictive description of embodiments thereof, given for the purpose of exemplification only, with reference to the accompanying drawings in which.

DETAILED DESCRIPTION

Figure 1:
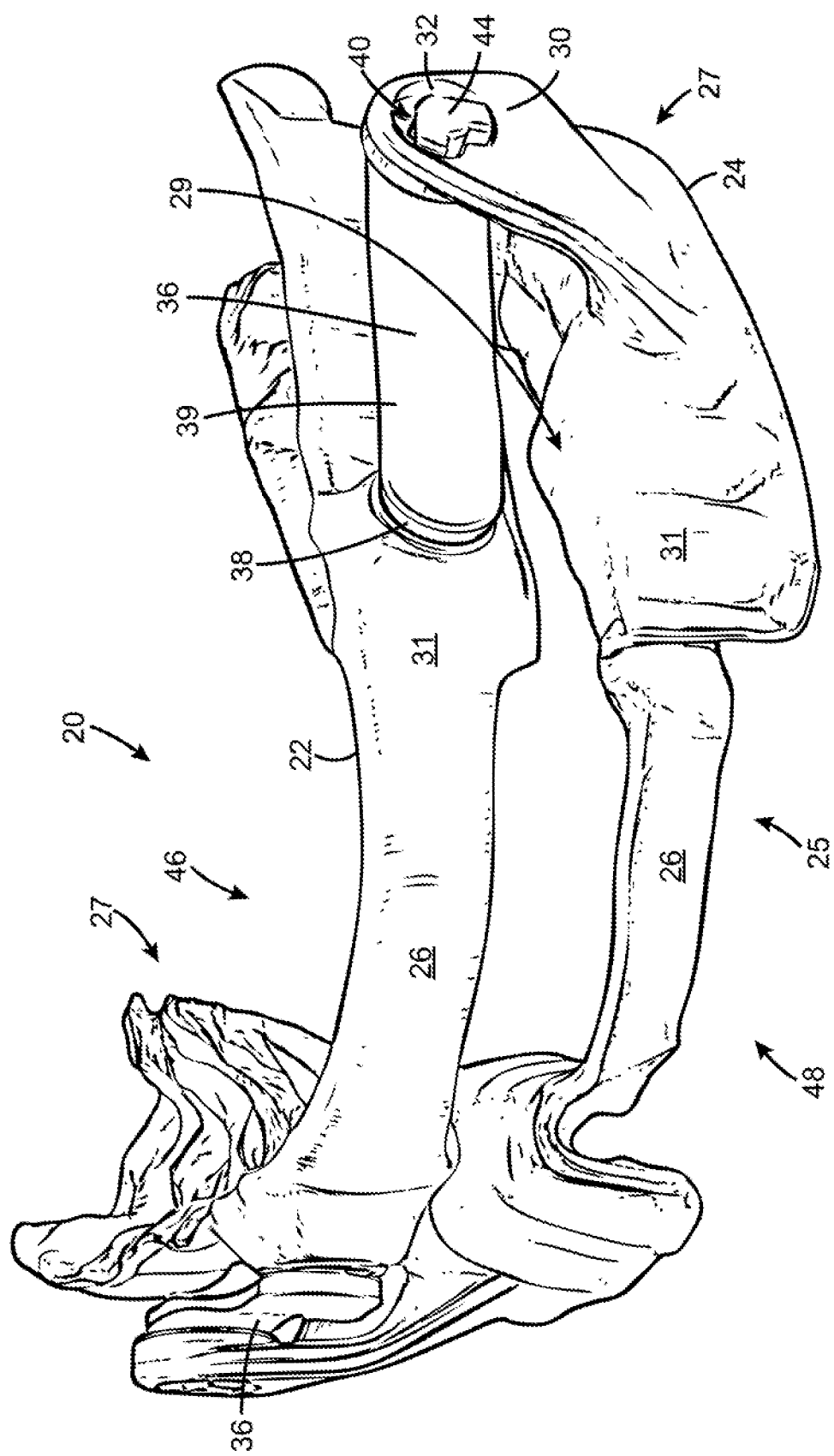
FIG. 1 is a front perspective view of a mandibular protrusion device in accordance with an embodiment.
Figure 2:
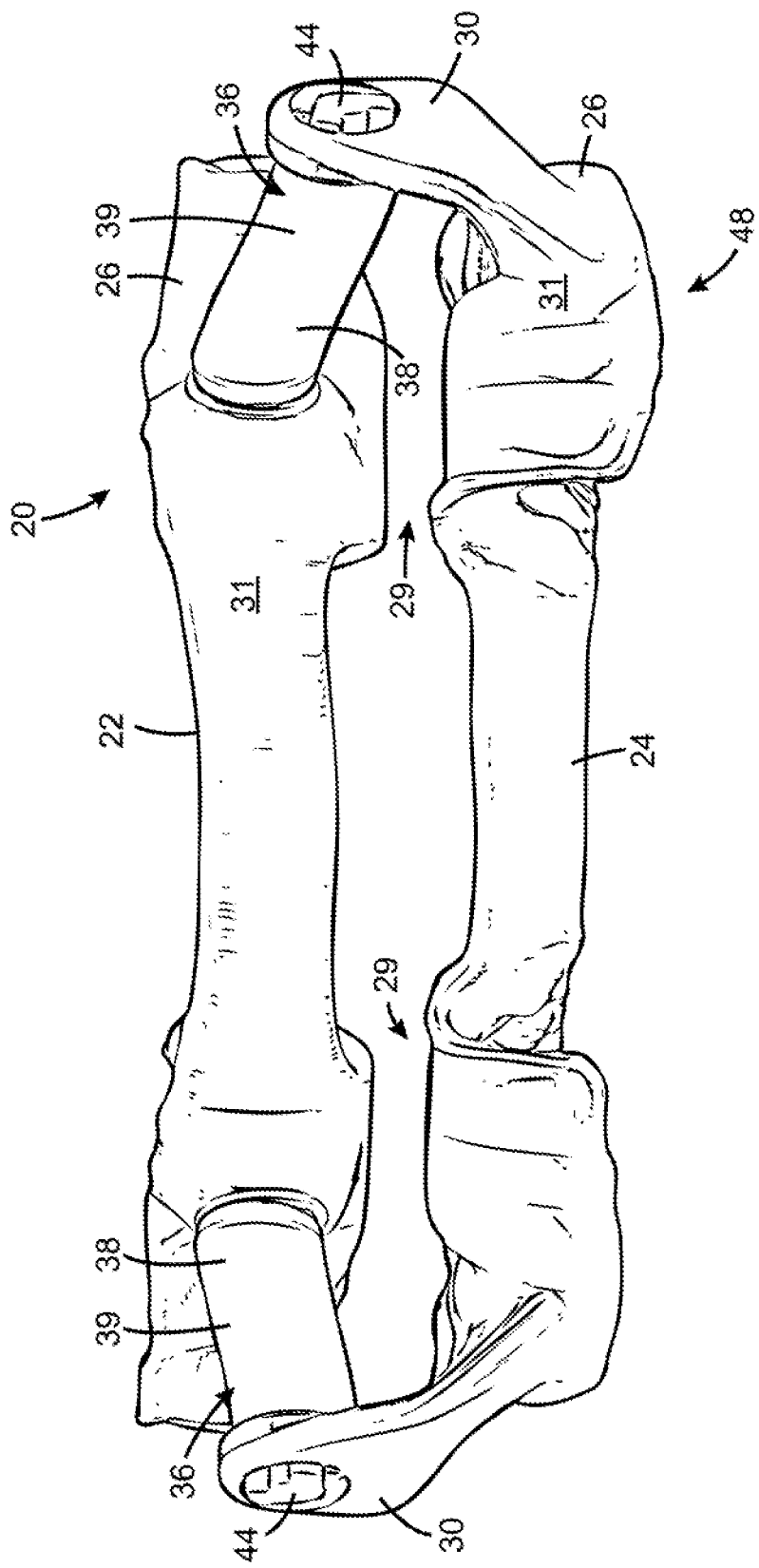
FIG. 2 is a front elevation view of the mandibular protrusion device shown in FIG. 1.
Figure 3:
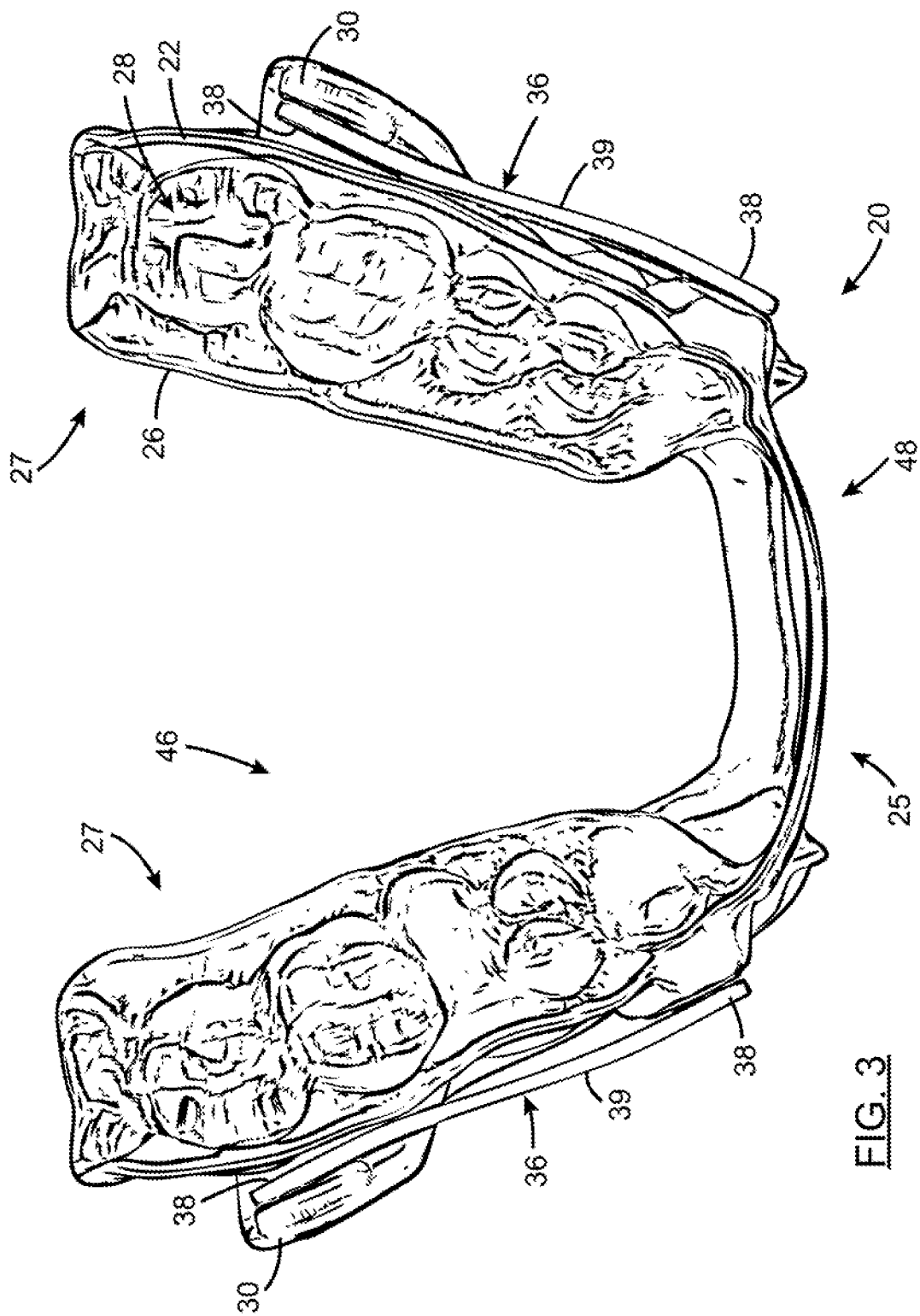
FIG. 3 is a top plan view of the mandibular protrusion device shown in FIG. 1.
Figure 4:
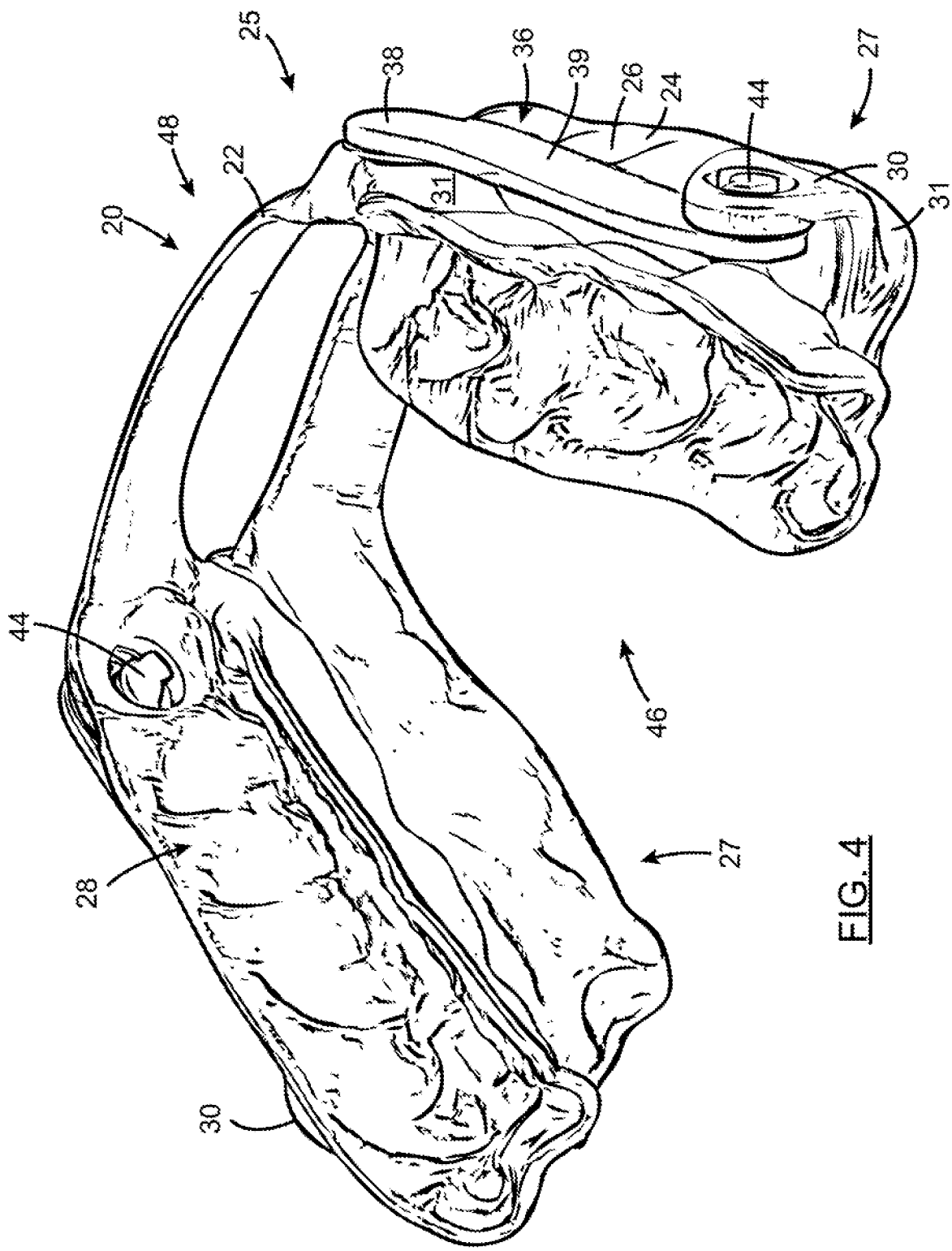
FIG. 4 is a rear perspective view of the mandibular protrusion device shown in FIG. 1.

In the following description, the same numerical references refer to similar elements. The embodiments, geometrical configurations, materials mentioned and/or dimensions shown in the figures or described in the present description are embodiments only, given solely for exemplification purposes.

Moreover, although the embodiments of the mandibular protrusion device and corresponding parts thereof consist of certain geometrical configurations as explained and illustrated herein, not all of these components and geometries are essential to the invention and thus should not be taken in their restrictive sense. It is to be understood, as also apparent to a person skilled in the art, that other suitable components and cooperation thereinbetween, as well as other suitable geometrical configurations, may be used for the mandibular protrusion device, as will be briefly explained herein and as can be easily inferred herefrom by a person skilled in the art. Moreover, it will be appreciated that positional descriptions such as "above", "below", "left", "right" and the like should, unless otherwise indicated, be taken in the context of the figures and should not be considered limiting.

Referring now to the drawings and, more particularly referring to FIGS. 1 to 4, there is shown a mandibular protrusion device (or intraoral orthosis) 20 in accordance with an embodiment. The mandibular protrusion device 20 includes two dental trays (or bite forms) and, more particularly a maxillary dental tray 22 (or upper dental tray) to be placed onto the user's maxilla and a mandibular dental tray 24 (or lower dental tray) to be placed onto the user's mandible. Each one of the dental trays 22, 24 has a wall 26 and defines a U-shaped dentition receiving cavity 28, which, in an embodiment, reflects the dentition of the intended user of the device 20. Each one of the dental trays is substantially U-shaped and has an anterior section 25 and two posterior sections 27 extending from opposite ends of the anterior section 25.

In an embodiment, the mandibular dental tray 24 has two flanges 30 extending upwardly from an outer side 31 of the wall 26 and located on opposite sides of the mandibular dental tray 24 in the posterior sections 27, i.e. at a rear end thereof. Each one of the flanges 30 has a mandibular dental tray aperture 32 defined therethrough. In an embodiment, the mandibular dental tray aperture 32 is defined in a section of the flanges 30 which extends above an upper section 29 of the wall 26 in the posterior sections 27. In an embodiment, the mandibular dental tray apertures 32 can be respectively located between teeth 34 to 38 and teeth 44 to 48 according to the FDI World Dental Federation notation. The mandibular dental tray apertures 32 are characterized by a predetermined shape, as will be described in more details below.

The maxillary dental tray 22 also has two maxillary dental tray apertures 34 defined therethrough. The maxillary dental tray apertures 34 are located on opposite sides of the maxillary dental tray 22 and extend through the outer side 31 of the wall 26. The maxillary dental tray apertures 34 are located anteriorly of the mandibular dental tray apertures 32, when the maxillary dental tray 22 and the mandibular dental tray 24 are superposed, in an operative configuration as will be described below. In an embodiment, the maxillary dental tray apertures 34 can be respectively located between teeth 12 to 16 and teeth 22 to 26 according to the FDI World Dental Federation notation. Similarly to the mandibular dental tray apertures 32, the maxillary dental tray apertures 34 are characterized by a predetermined shape, as will also be described in more details below.

Figure 5:
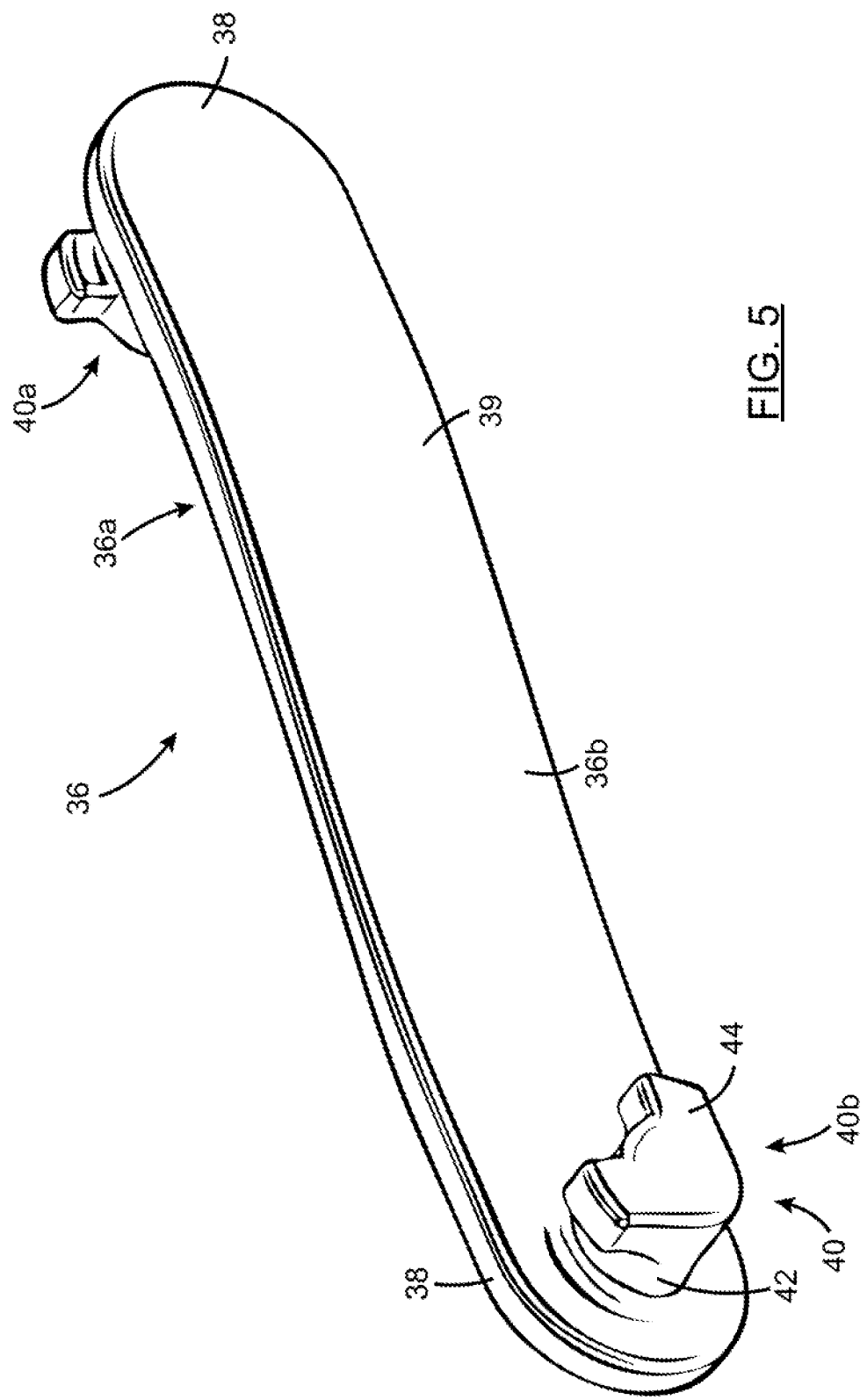
FIG. 5 is a perspective view of a lateral link of the mandibular protrusion device shown in FIG. 1.
Figure 6:
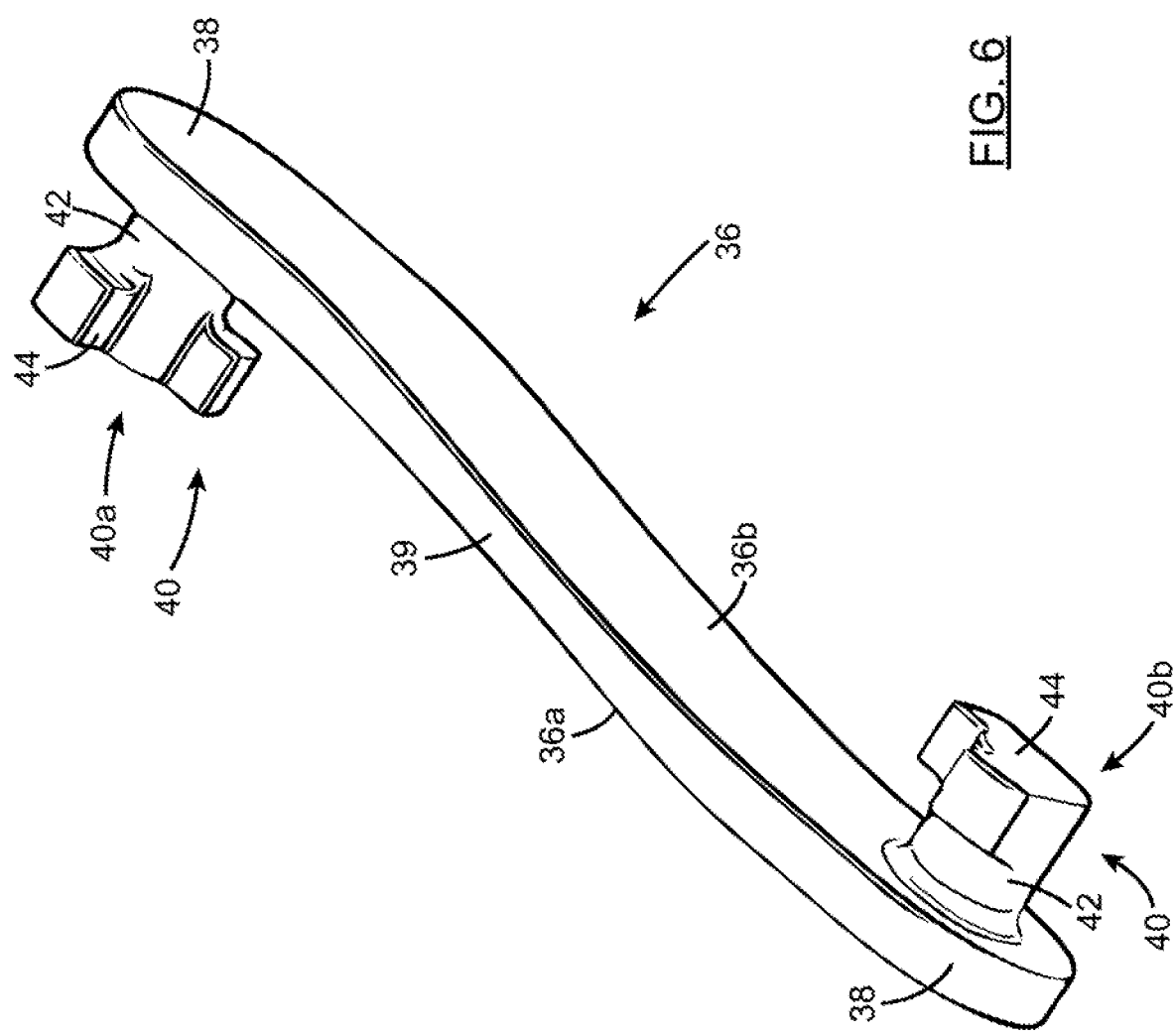
FIG. 6 is a perspective view of a lateral link of a mandibular protrusion device according to an embodiment where the lateral link is thicker along sections of the elongated portion and towards ends thereof.
Figure 7:
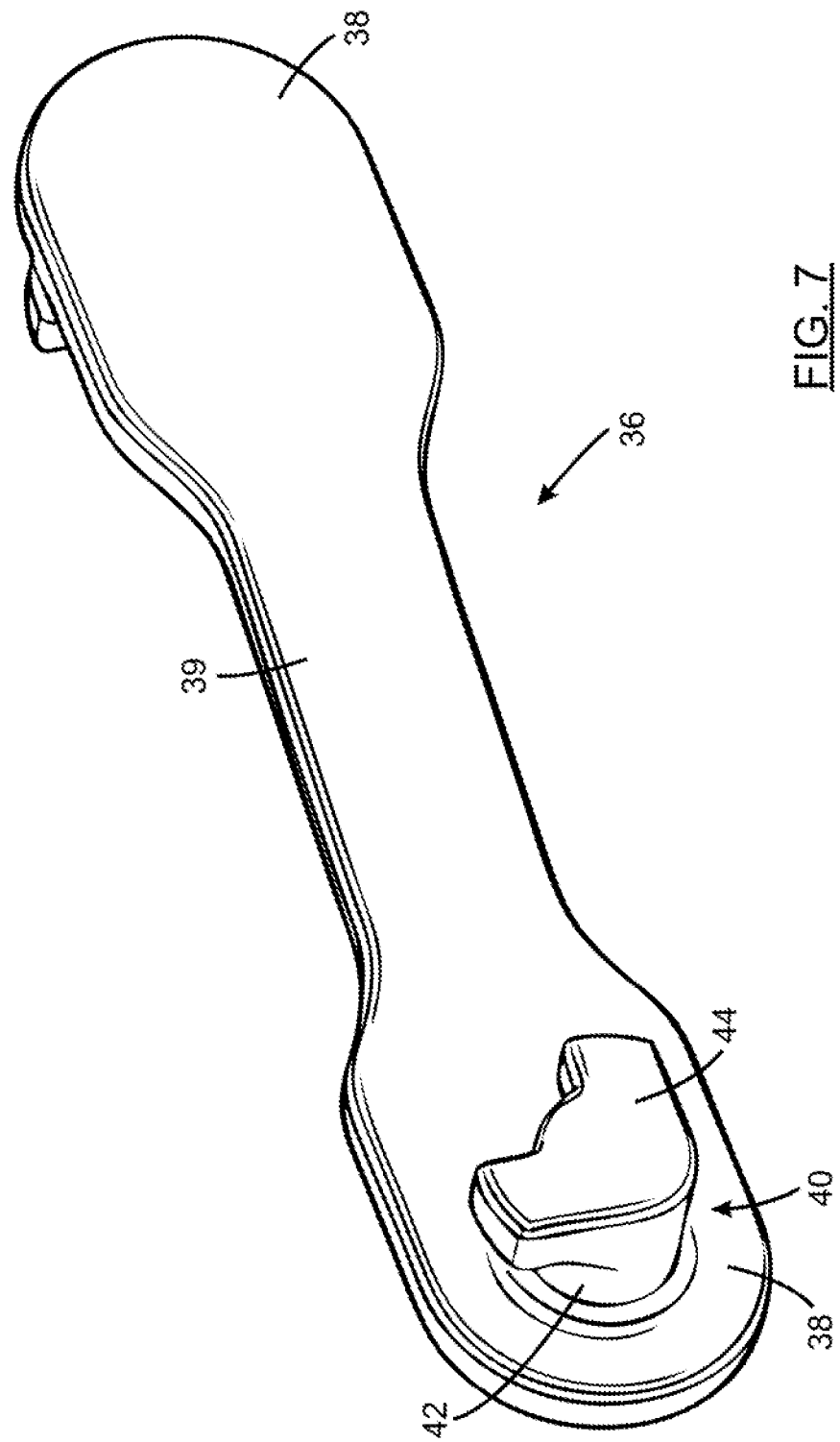
FIG. 7 is a perspective view of a lateral link of a mandibular protrusion device according to an embodiment where the lateral link is narrower in the central section of the elongated portion.

Referring to FIGS. 1 to 7, the mandibular protrusion device 20 also includes two lateral links 36 configured to pivotally connect the maxillary dental tray 22 and the mandibular dental tray 24 to one another. As shown in FIGS. 5 to 7, each one of the lateral links 36 has two ends 38, defined at opposite ends of an elongated portion 39. The ends 38 of the lateral links 36 also are engageable with a respective one of the maxillary dental tray 22 and the mandibular dental tray 24. The maxillary dental tray 22, the mandibular dental tray, and the lateral links 36 are configured such that when the lateral links 36 are connected to the dental trays 22, 24, the user's mandible is moved forward.

The lateral links 36 are flexible members. As can be seen in FIGS. 5 to 7, the lateral links 36 could present different configurations. In the embodiment shown in FIG. 5, the lateral link 36 has a substantially uniform width and thickness. In the embodiment shown in FIG. 6, the lateral link 36 is characterized by an overall thicker profile than in the embodiment shown in FIG. 5, including thicker sections of the elongated portion 39 and thicker ends 38. For instance, this lateral link 36 can be suitable for users experimenting high levels of bruxism. In the embodiment shown in FIG. 7, the lateral link 36 is narrower in a central portion of the elongated portion 39 than at the ends 38. For instance, this lateral link 36 can be suitable for users having a weak jaw musculature. In all of the illustrated embodiments, the elongated portion 39 has a curvature defined therein, i.e. it is slightly curved, such as to better adapt to the morphology of the user and provide some resilience when stretched. However, it is appreciated that, in an alternative embodiment, the shape of the lateral links 36, including their elongated portion 39 and their ends 38, can vary from the embodiments shown.

Each one of the ends 38 of the lateral links 36 includes a pivot member 40 engageable with the mandibular dental tray apertures 32 and the maxillary dental tray apertures 34. In the illustrated embodiment, a first pivot member 40a protrudes on a first side 36a and a second pivot member 40b protrudes on a second side 36b of each lateral link 36. More particularly, the pivot members 40 have a pivot portion 42 and an enlarged head 44. The shape of the enlarged heads 44 corresponds to the shape of the mandibular dental tray apertures 32 and the maxillary dental tray apertures 34 such as to be insertable therein. The pivot portion 42 is smaller in cross-section than the apertures 32, 34 in order to pivot freely therein.

In the embodiment shown, the mandibular dental tray apertures 32, the maxillary dental tray apertures 34 and the enlarged heads 44 are substantially L-shaped. The pivot portions 42 are connected to their respective enlarged head 44 at the junction of the two arms of the L-shaped enlarged heads 44. In the embodiment shown, the pivot portions 42 are cylindrical members with a substantially circular cross-section. One skilled in the art would understand that the mandibular dental tray apertures 32, the maxillary dental tray apertures 34 and the enlarged heads 44 could also have other particular predetermined shape.

Figure 8:
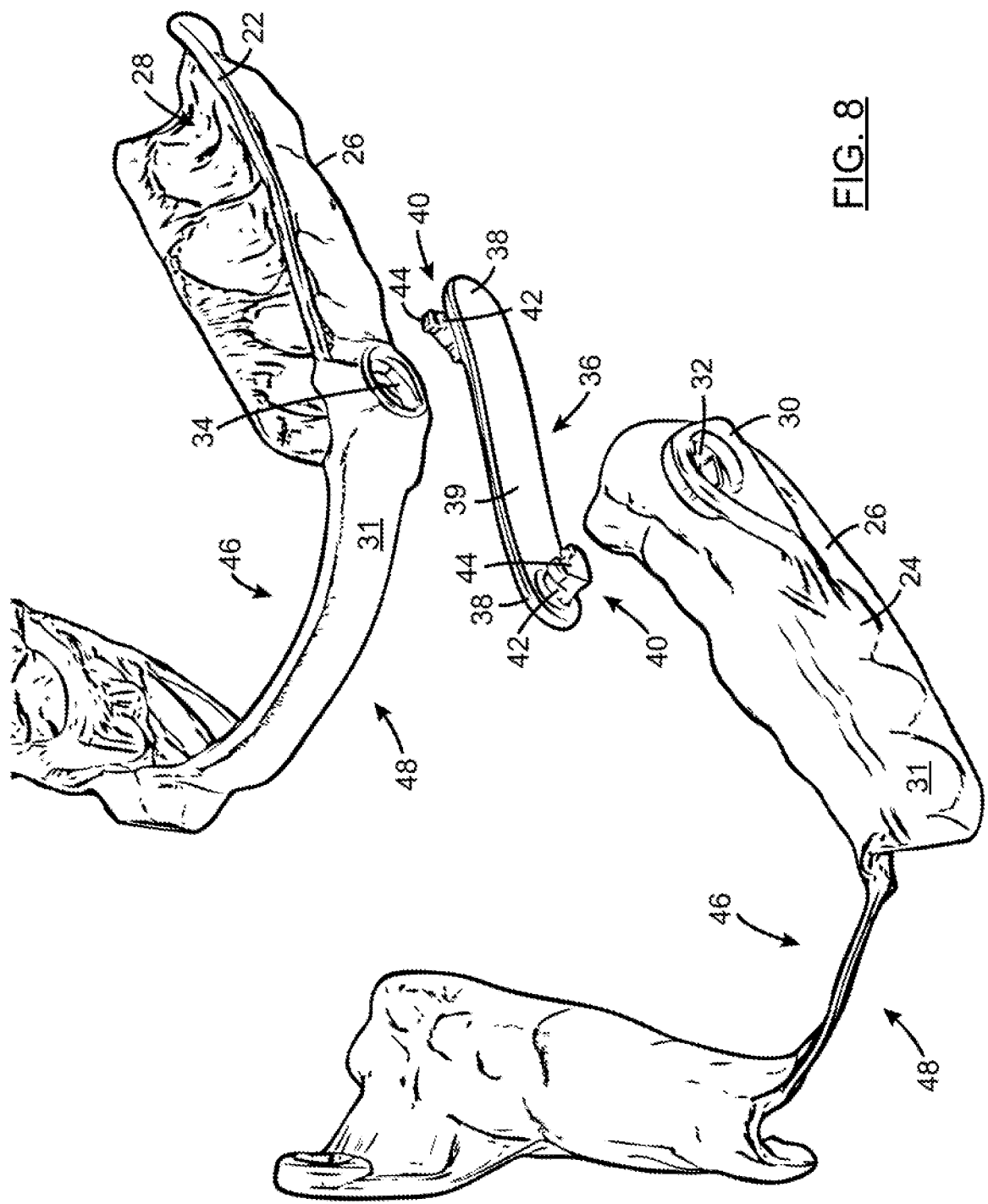
FIG. 8 is a front perspective view of the mandibular protrusion device shown in FIG. 1, wherein the mandibular protrusion device is in an inoperative configuration and one of the lateral links is detached from the dental trays.
Figure 9:
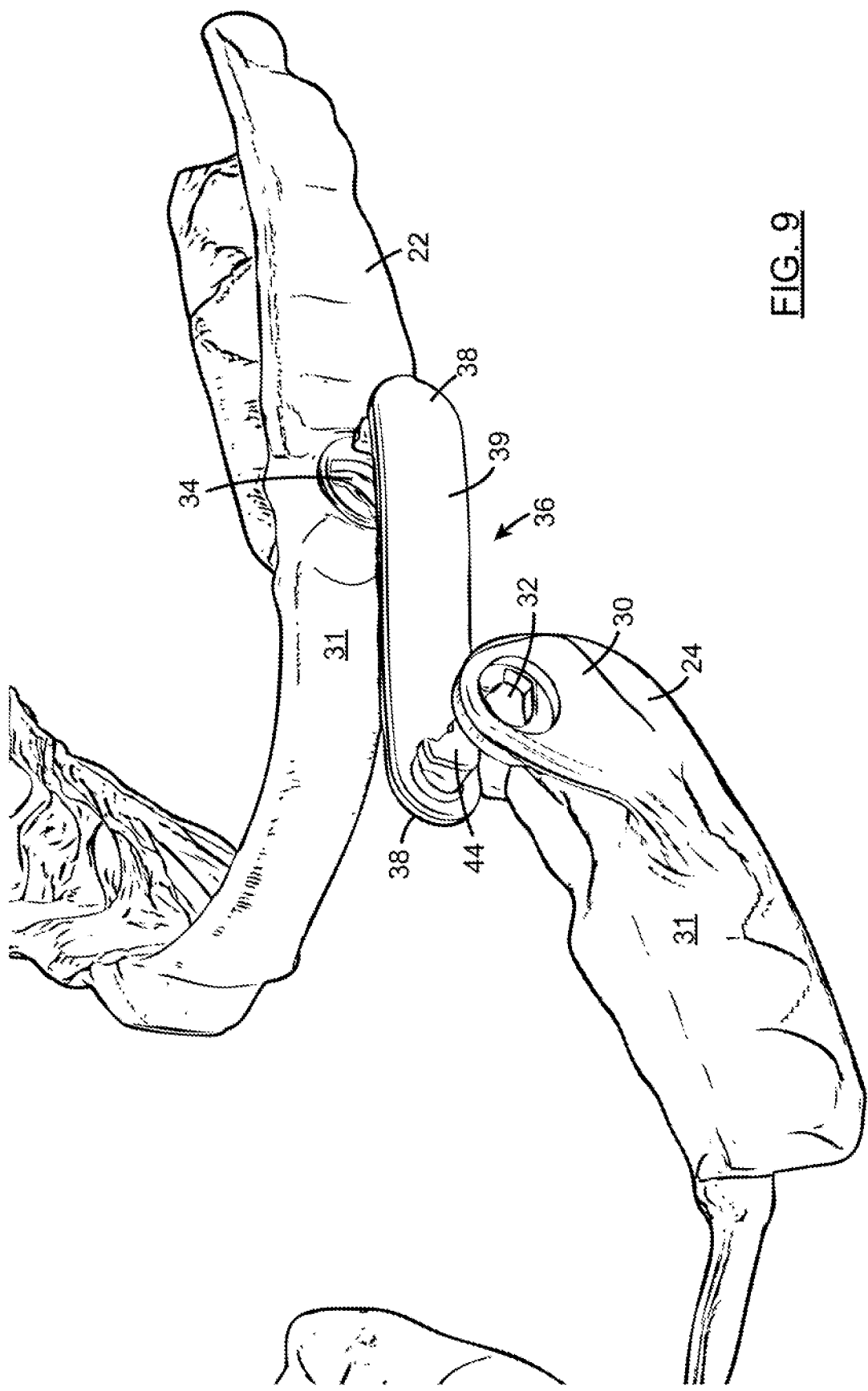
FIG. 9 is a side elevation view of the mandibular protrusion device shown in FIG. 1, wherein the mandibular protrusion device is in an inoperative configuration and one of the lateral links is configured to be engaged with the dental trays.

Thus, as shown in FIGS. 8 and 9, the enlarged heads 44 can be inserted into or disengaged from the dental tray apertures 32 and/or the maxillary dental tray apertures 34 in a single configuration, i.e. only in a configuration wherein the two arms of the "L" of the enlarged heads 44 are aligned (or "substantially in register") with the two arms of the "L" of the mandibular dental tray apertures 32 and/or the maxillary dental tray apertures 34. When the enlarged heads 44 are inserted in the mandibular dental tray apertures 32 and/or the maxillary dental tray apertures 34 and extend past the flanges 30 and/or the wall 26, the lateral links 36 can freely pivot in the apertures 32, 34.

Furthermore, in the embodiment shown, a first one of the arms of the L-shaped enlarged heads 44 extends substantially parallel to the elongated portion 39 of the lateral links 36. Thus, the first arms of the L-shaped enlarged heads 44 of the lateral links 36 are oriented towards one another. The second ones of the arms of the L-shaped enlarged heads 44 of the lateral links 36 extends in the same direction and substantially perpendicularly to the first arms.

In the embodiment shown, the two lateral links 36 of the mandibular protrusion device 20 are identical. However, in an alternative embodiment, the two lateral links 36 of a device 20 could be different from one another. Moreover, the shape of the pivot portions 42 and/or the enlarged heads 44 can vary from the embodiment shown, provided that the shape of the enlarged heads 44 and the shape of the corresponding mandibular dental tray apertures 32 and/or maxillary dental tray apertures 34 are selected in a manner such that the enlarged heads 44 can be inserted into or disengaged from the apertures 32, 34 in a non-operative configuration. In an embodiment, the non-operative configuration in which the enlarged heads 44 can be inserted into or disengaged from the apertures 32, 34 is a single configuration.

Furthermore, in the embodiment shown, the pivot members 40 and the corresponding mandibular dental tray apertures 32 and maxillary dental tray apertures 34 all have the same shape. However, in an alternative embodiment, the pivot members 40 for the maxillary dental tray 22 could differ from the pivot members 40 for the mandibular dental tray 24. Similarly, the pivot members 40 and the corresponding mandibular dental tray apertures 32 and maxillary dental tray apertures 34 of a left side of the mandibular protrusion device 20 could differ from the pivot members 40 and the corresponding mandibular dental tray apertures 32 and maxillary dental tray apertures 34 of a right side of the mandibular protrusion device 20.

Figure 14:
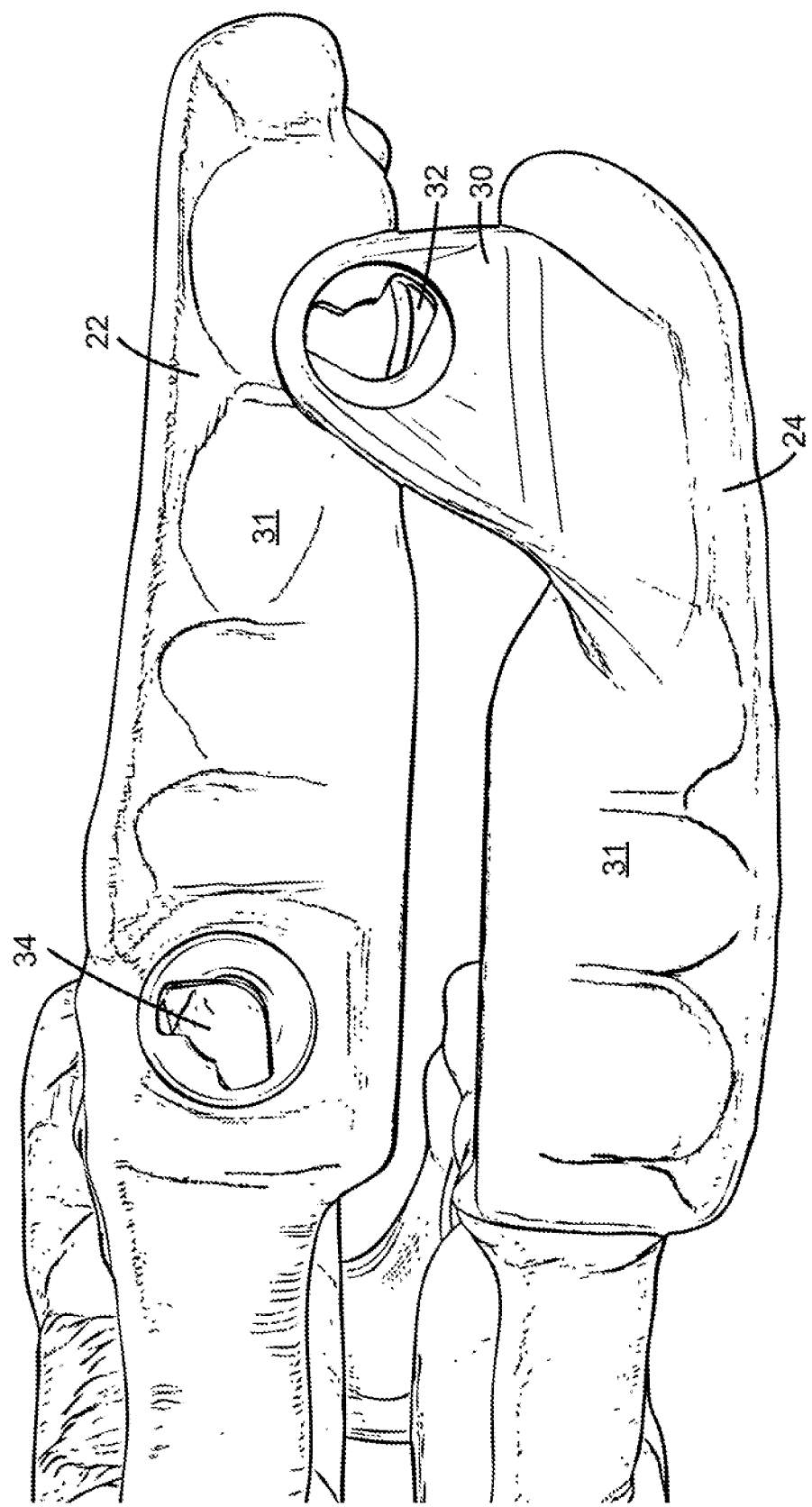
FIG. 14 is a perspective view, enlarged, of a right side of the mandibular protrusion device shown in FIG. 1, without the lateral links.
Figure 15:
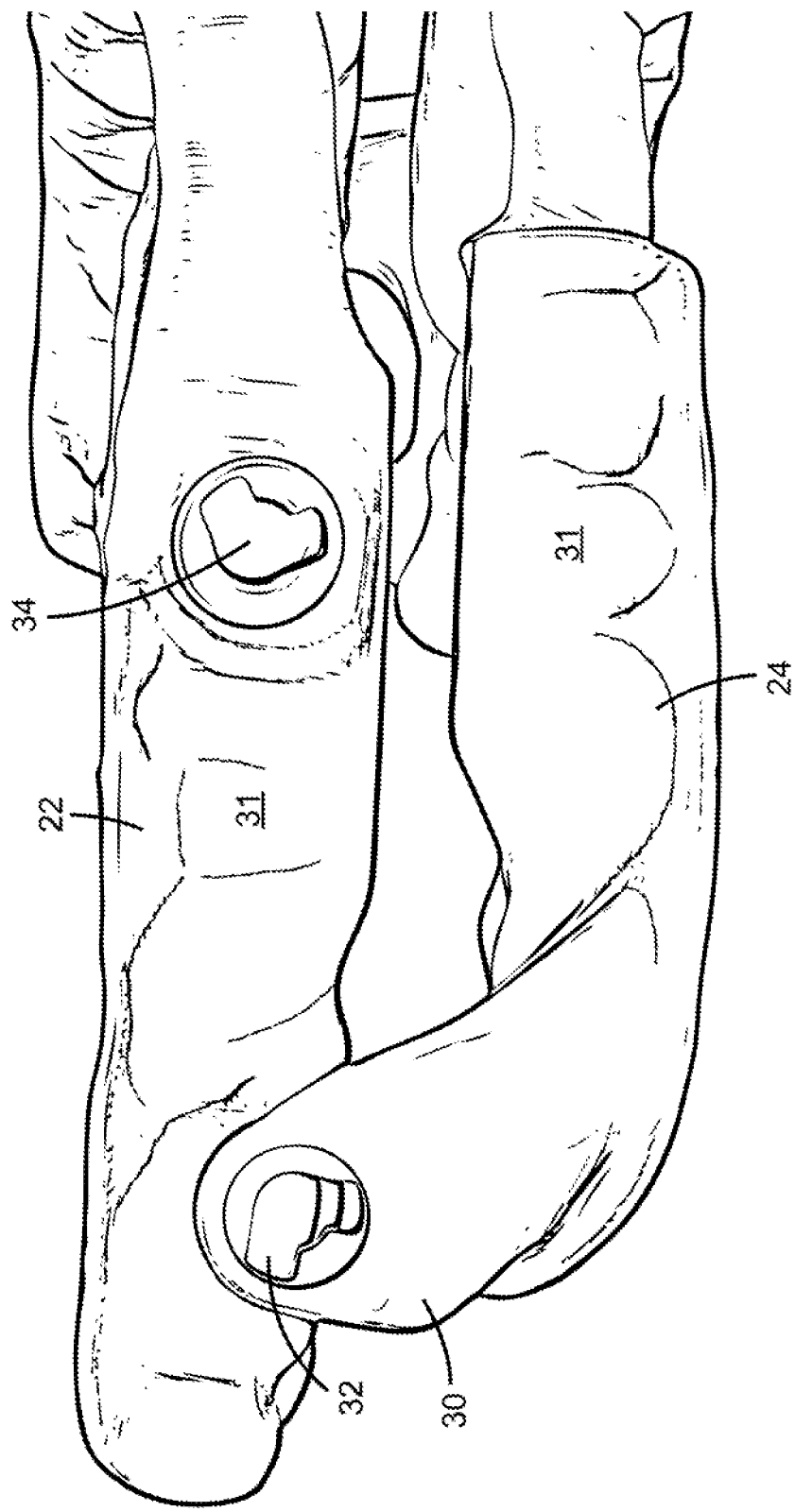
FIG. 15 is a perspective view, enlarged, of a left side of the mandibular protrusion device shown in FIG. 1, without the lateral links.

Still referring to the embodiment shown, and more particularly to FIGS. 14 and 15, when the maxillary dental tray 22 and the mandibular dental tray 24 are superposed the right side L-shaped mandibular dental tray aperture 32 is configured with a first one of the arms extending substantially downwardly and rearwardly and a second one of the arms extending substantially upwardly and rearwardly. The left side L-shaped mandibular dental tray aperture 32 is configured with a first one of the arms extending substantially downwardly and rearwardly and a second one of the arms extending substantially rearwardly and upwardly. The right side L-shaped maxillary dental tray aperture 34 is configured with a first one of the arms extending substantially upwardly and forwardly and a second one of the arms substantially extending downwardly and forwardly. The left side L-shaped maxillary dental tray aperture 34 is configured with a first one of the arms extending substantially forwardly and upwardly and a second one of the arms extending substantially downwardly and forwardly.

In the embodiment shown, the pivot members 40 of the lateral links 36 are engaged with the mandibular dental tray 24 by inserting the pivot members 40 from an inner side 46 towards an outer side 48 of the tray 24. On the opposite, the pivot members 40 of the lateral links 36 are engaged with the maxillary dental tray 22 by inserting the pivot members 40 from the outer side 48 towards the inner side 46 of the tray 22. It is appreciated that, in an alternative embodiment, the pivot members 40 of the lateral links 36 could be engaged with the mandibular dental tray 24 by inserting the pivot members 40 from the outer side 48 towards the inner side 46 of the tray 22. For instance and without being limitative, this configuration could occur if the mandibular dental tray 24 is free of flanges 30 and the lateral links 36 are engaged directly with the mandibular dental tray 24, as it is shown in the accompanying figures for the maxillary dental tray 22.

Furthermore, in an implementation, the maxillary dental tray 22 can include flanges extending downwardly and the maxillary dental tray apertures 34 could be defined in the flanges. The pivot members 40 of the lateral links 36 could be engaged with the maxillary dental tray 22 by inserting the pivot members 40 from the inner side 46 towards the outer side 48 of the tray 22.

In the embodiment shown, the mandibular dental tray apertures 32 and maxillary dental tray apertures 34 are positioned in a manner such that the elongated portion 39 of the lateral links 36 extend substantially horizontally when the maxillary dental tray 22 rests (or abuts) the mandibular dental tray 24, i.e. the mandibular protrusion device is in the operative configuration, as shown in FIGS. 1 to 4. In an embodiment, the orientation of the lateral links 36 when the maxillary dental tray 22 rests (or abuts) the mandibular dental tray 24 is substantially parallel to a contact plan between the maxillary dental tray 22 and the mandibular dental tray 24 in the posterior sections 27.

Figure 13:
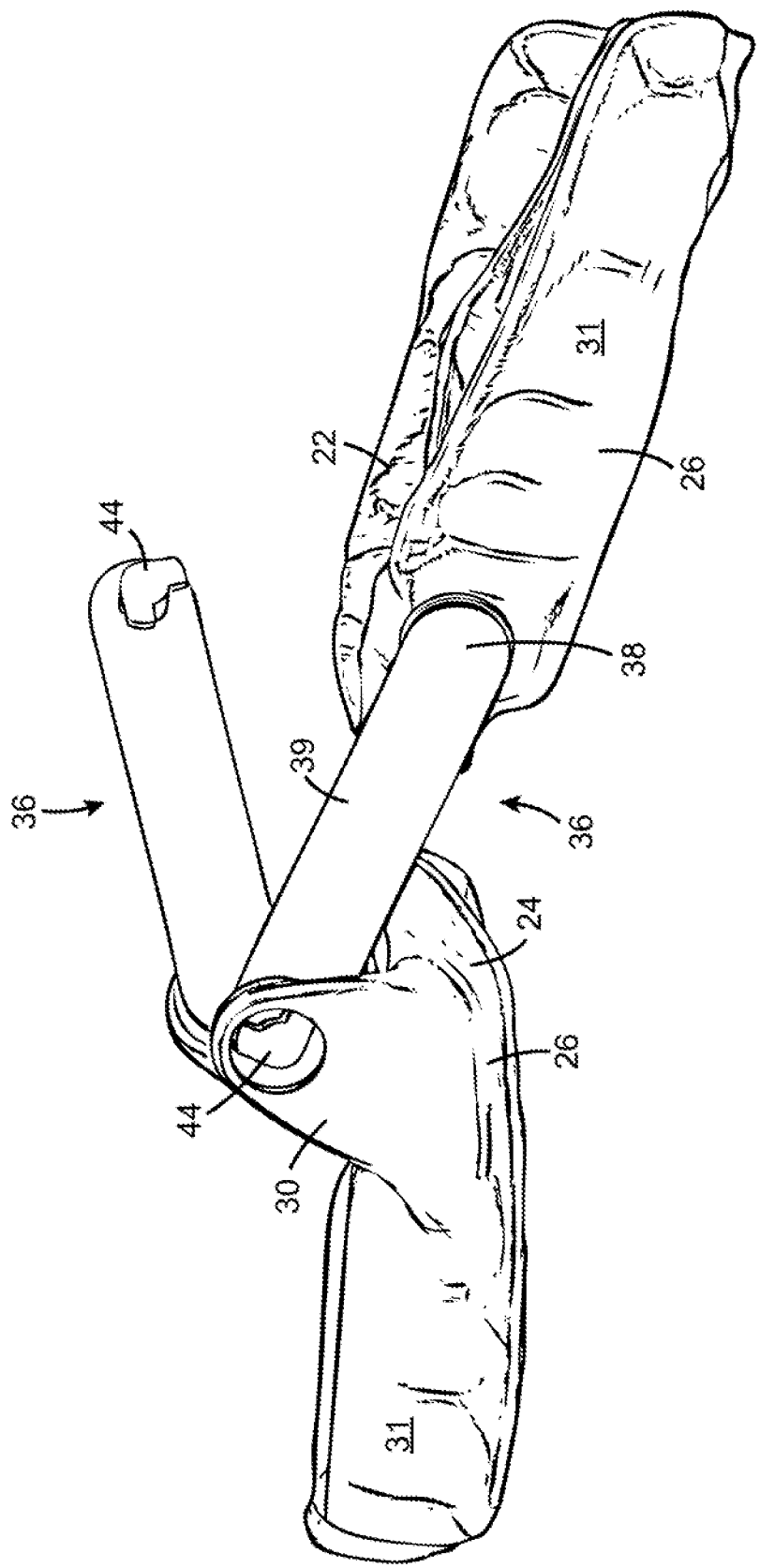
FIG. 13 is a perspective view of the mandibular protrusion device shown in FIG. 1, wherein the mandibular dental tray and the maxillary dental tray are configured in an engagement/disengagement configuration and the left side lateral link is positioned in its engagement/disengagement configuration.

Referring to FIGS. 8 to 13, the mandibular dental tray apertures 32 and maxillary dental tray apertures 34 are also configured in a manner such that, in order to engage and disengage the lateral links 36 from the apertures 32, 34, the maxillary dental tray 22 must be pivoted rearwardly from its operative position into an engagement/disengagement configuration. In the illustrated embodiment, the engagement/disengagement configuration for the left side lateral link is different than the engagement/disengagement configuration for the right side lateral link. As can be seen in FIG. 13, in the illustrated embodiment there is approximately a 30° offset between the engagement/disengagement configurations of the two lateral links 36. The left side lateral link has an engagement/disengagement configuration at about 200° and the right side lateral link has an engagement/disengagement configuration at about 170°, with respect to the normal and operative configuration wherein the two trays 22, 24 are superposed. One skilled in the art will appreciate that, in an alternative embodiment, the engagement/disengagement configuration of the left side lateral link and the right side lateral link could be inverted.

Moreover, in an alternative embodiment the offset between the engagement/disengagement configurations of the two lateral links 36 could be smaller or greater than 30° and could range between 0° and 90°. For example and without being limitative, in an embodiment, the left side lateral link can have an engagement/disengagement configuration at about 225° and the right side lateral link can have an engagement/disengagement configuration at about 135°, with respect to the normal and operative configuration wherein the two trays 22, 24 are superposed.

It will be understood that, in another alternative embodiment, the engagement/disengagement configuration could be the same for the left side lateral link and the right side lateral link, i.e. there could be no offset between the engagement/disengagement configurations of the two lateral links 36. For example and without being limitative, the maxillary dental tray 22 could be configured in a configuration wherein it is positioned behind and at the same height than the mandibular dental tray 24, i.e. it is rotated rearwardly about 180° from the operative configuration, to be configured in the engagement/disengagement configuration.

The engagement/disengagement configuration wherein the enlarged heads 44 can be inserted into or disengaged from the mandibular dental tray apertures 32 and maxillary dental tray apertures 34 corresponds to a non-operative configuration, i.e. a configuration that is not reached when the device is worn or in normal use. As mentioned above, in the embodiment shown, the engagement/disengagement configuration corresponds to a configuration wherein the maxillary dental tray 22 is rotated rearwardly with respect to the mandibular dental tray 24. For instance, the maxillary dental tray 22 can be rotated rearwardly between 90°, wherein the lateral links extend substantially vertically and upwardly from the mandibular dental tray 24, and 270°, wherein the lateral links extend substantially vertically and downwardly from the mandibular dental tray 24, from the operative configuration to be configured in the engagement/disengagement configuration. Furthermore, it corresponds to a configuration that cannot be reached during conventional washing operation of the mandibular protrusion device 20.

Figure 10:
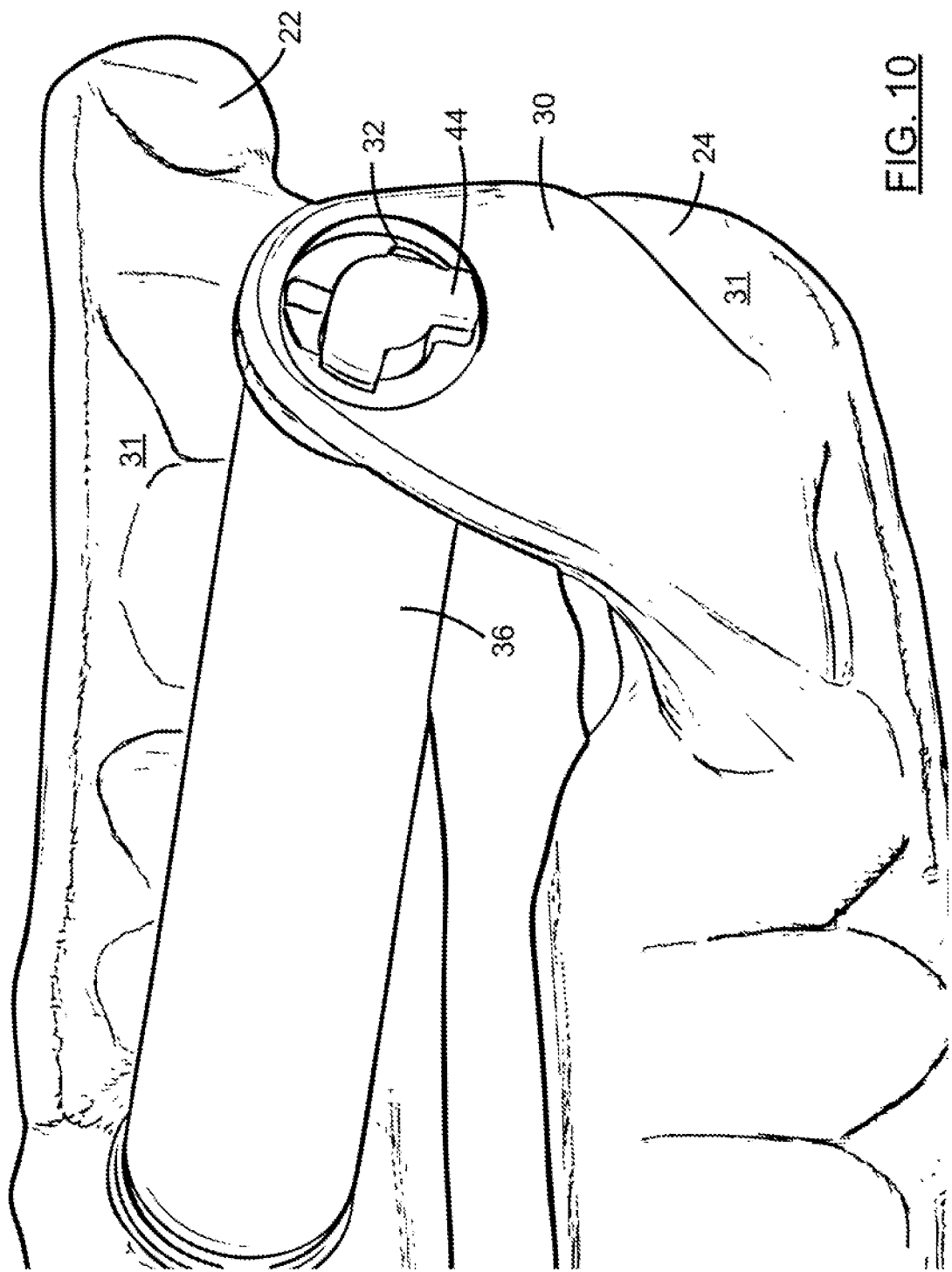
FIG. 10 is a perspective view, enlarged, of a rear end of the lateral link shown in FIG. 5, engaged with the mandibular dental tray.
Figure 11:
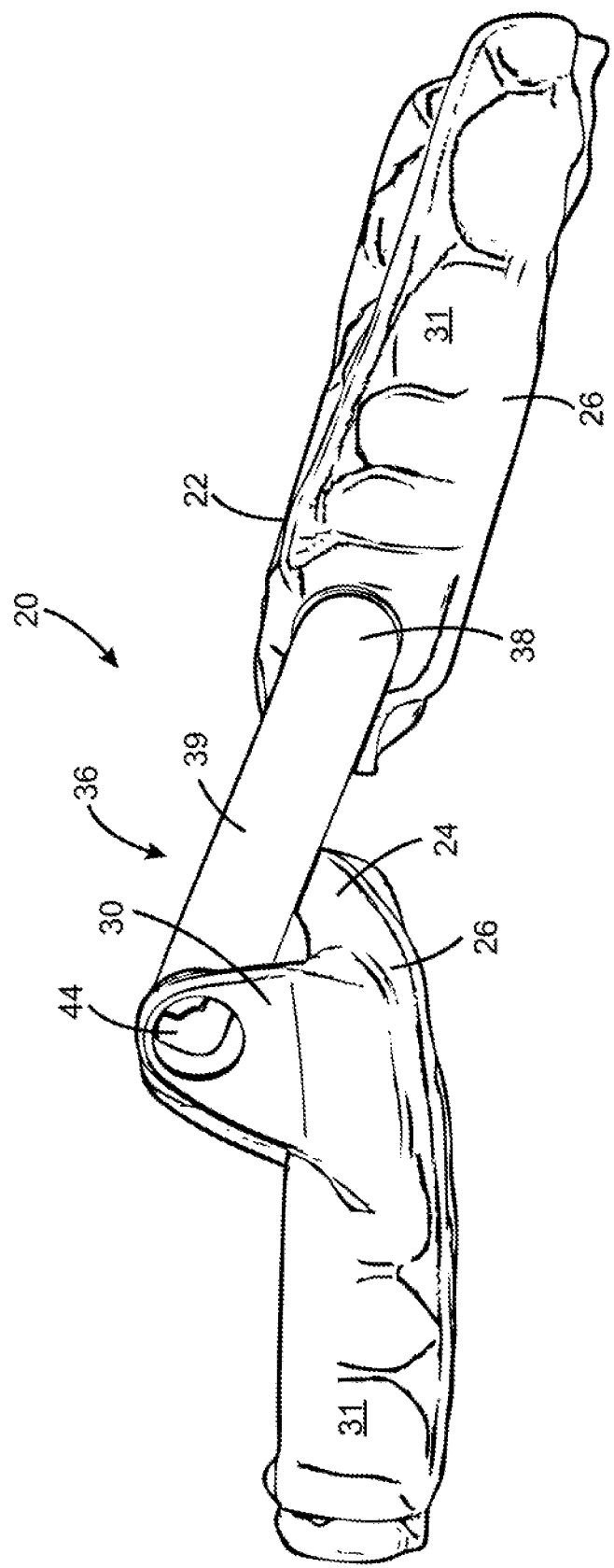
FIG. 11 is a perspective view of the mandibular protrusion device shown in FIG. 1, wherein the mandibular dental tray and the maxillary dental tray are configured in an engagement/disengagement configuration for a right side lateral link.
Figure 12:
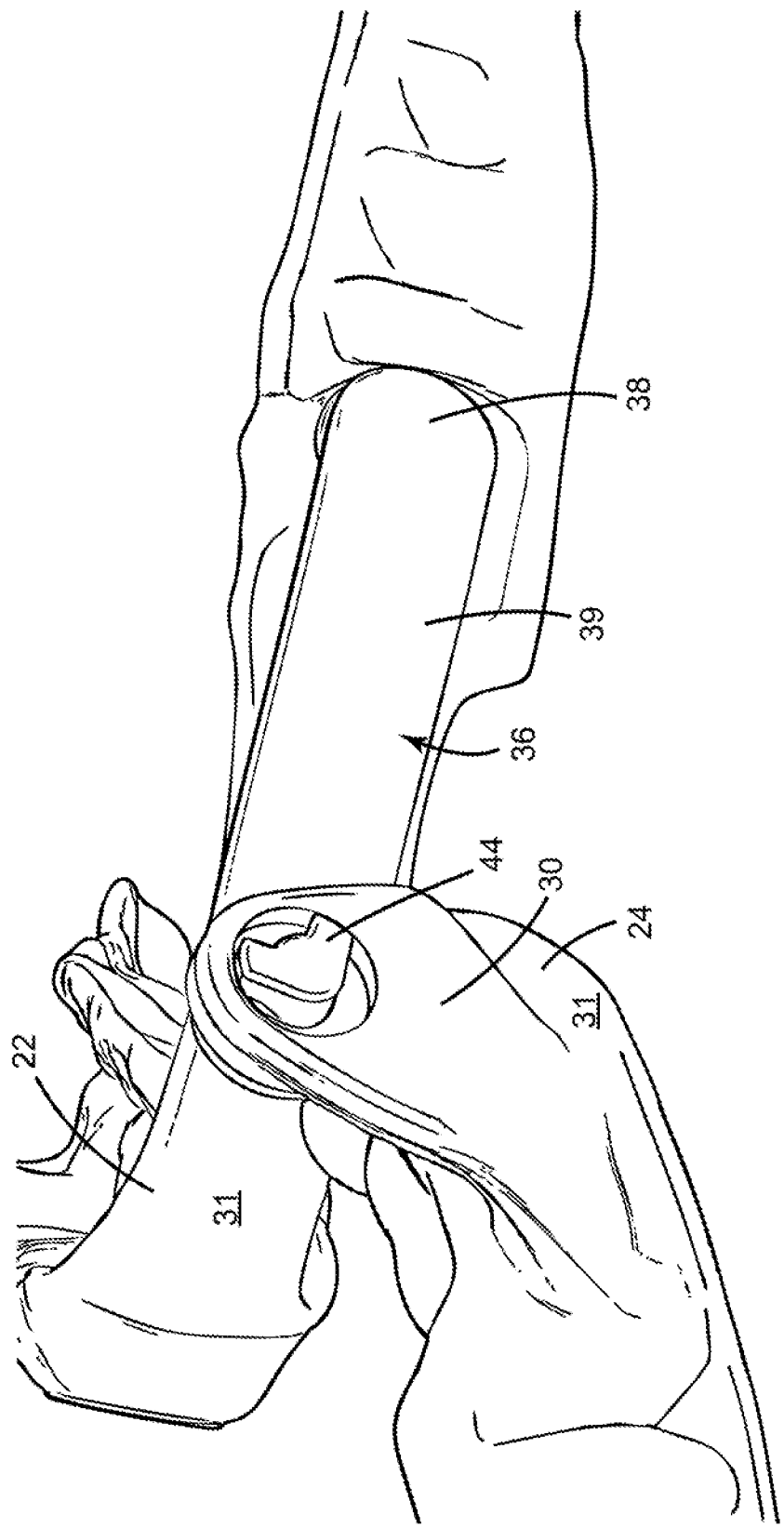
FIG. 12 is a perspective view, enlarged, of the mandibular protrusion device showing the lateral link when the mandibular dental tray and the maxillary dental tray are configured in the engagement/disengagement configuration for the right side lateral link.

In the operative configuration wherein the maxillary dental tray 22 and the mandibular dental tray 24 are superposed, the lateral links 36 are prevented from disengagement from the dental trays 22, 24 since the enlarged heads 44 are not aligned (or substantially in register) with their apertures 32, 34 as shown in FIG. 10.

In an alternative embodiment (not shown), the device 20 can have more than one engagement/disengagement configuration, i.e. the enlarged heads 44 can be inserted into or disengaged from the apertures 32, 34 in more than one configuration, provided that the configurations correspond to non-operative configurations, i.e. configurations that are not reached when the device is worn or in normal use.

In the embodiment shown, the dental trays 22, 24 include the female members, i.e. the mandibular dental tray apertures 32 and maxillary dental tray apertures 34, in which the male members of the lateral links 36 are engageable, i.e. the pivot members 40. In an alternative embodiment (not shown), the dental trays 22, 24 can include the male members, i.e. the pivot members which protrude outwardly therefrom, and the lateral links 36 can include the complementary female members, i.e. apertures defined therethrough. In this embodiment, the shape of the apertures can be a predetermined shape which corresponds to the predetermined shape of the pivot members and, more particularly, to the shape of an enlarged head thereof. The complementary male and female members can be configured and positioned in a manner such that they are engageable and disengageable from one another in one or several non-operative configurations, i.e. configurations that are not reached when the device is worn or in normal use. In an embodiment, the complementary male and female members can be engageable and disengageable from one another in a single configuration, which can be a configuration that is not reached when the device is worn or in normal use.

Several alternative embodiments and examples have been described and illustrated herein. The embodiments of the invention described above are intended to be exemplary only. A person of ordinary skill in the art would appreciate the features of the individual embodiments, and the possible combinations and variations of the components. A person of ordinary skill in the art would further appreciate that any of the embodiments could be provided in any combination with the other embodiments disclosed herein. It is understood that the invention may be embodied in other specific forms without departing from the spirit or central characteristics thereof. The present examples and embodiments, therefore, are to be considered in all respects as illustrative and not restrictive, and the invention is not to be limited to the details given herein. Accordingly, while the specific embodiments have been illustrated and described, numerous modifications come to mind without significantly departing from the spirit of the invention. The scope of the invention is therefore intended to be limited solely by the scope of the appended claims.

The invention claimed is:

1. A mandibular protrusion device having a right side and a left side, the mandibular protrusion device comprising:
    a maxillary dental tray having a wall with an outer side, an anterior section, and two spaced-apart posterior sections, the wall defining a U-shaped dentition receiving cavity;
    a mandibular dental tray having a wall with an outer side, an anterior section, and two spaced-apart posterior sections, the wall defining a U-shaped dentition receiving cavity, the mandibular dental tray further comprising two flanges extending upwardly from a respective one of the posterior sections and outwardly from the outer side of the wall, wherein a lateral link receiving channel is defined between each one of the two flanges and the outer side of the wall of the mandibular dental tray; and
    two lateral links, each one of the lateral links having an elongated portion with an anterior end removably engageable with the maxillary dental tray, a posterior end opposed to the anterior end, a dental-tray facing face, and a flange-facing face opposed to the dental-tray facing face, the posterior end being removably engageable with a respective one of the flanges of the mandibular dental tray, and located in a respective one of the lateral link receiving channels when engaged with the respective one of the flanges of the mandibular dental tray;
    two male members provided on each one of the right side and the left side of the mandibular protrusion device and two female members provided on each one of the right side and the left side of the mandibular protrusion device, the female members being complementary in shape to the male members, the female members and the male members being provided on the anterior section of the maxillary dental tray, the flanges of the mandibular dental tray, and the anterior ends and the posterior ends of the two lateral links to detachably engage the two lateral links with the mandibular dental tray and the maxillary dental tray at the posterior ends and the anterior ends; and
    wherein a first one and a second one of the male members provided on each one of the right side and the left side of the mandibular protrusion device protrude respectively towards and away from the outer side of the walls of the maxillary and mandibular dental trays when the lateral links are engaged therewith; and wherein the complementary male and female members are engageable and disengageable from one another in at least one engagement/disengagement configuration that is reached by pivoting at least one of the maxillary dental tray and the mandibular dental tray with respect to the other one and when the anterior section of the maxillary dental tray is located posteriorly of the flanges of the mandibular dental tray.

2. The mandibular protrusion device of claim 1, wherein the engagement/disengagement configuration is a single configuration for each one of the two lateral links.

3. The mandibular protrusion device of claim 2, wherein the two lateral links comprise a right-side lateral link and a left-side lateral link, and wherein the engagement/disengagement configuration is different for the right-side lateral link and the left-side lateral link and an offset between the engagement/disengagement configurations of the two lateral links is greater than 30°.

4. The mandibular protrusion device of claim 3, wherein the complementary male and female members are substantially L-shaped and the engagement/disengagement configuration for the right-side lateral link is reached by rotating one of the maxillary dental tray and the mandibular dental tray to a first angle and the engagement/disengagement configuration for the left-side lateral link is reached by rotating one of the maxillary dental tray and the mandibular dental tray to a second angle different from the first angle.

5. The mandibular protrusion device of claim 2, wherein each one of the male members comprises a pivot portion rotatable into a corresponding one of the complementary female members when engaged together and connected to a substantially L-shaped enlarged head.

6. The mandibular protrusion device of claim 5, wherein each one of the female members comprises an L-shaped aperture and the L-shaped enlarged head of each one of the male members is defined by two arms intersecting each other at an angle with the pivot portion being connected to the respective enlarged head at the intersection of the two arms, and each one of the enlarged head is insertable into or disengageable from the respective one of the L-shaped apertures solely in the engagement/disengagement configuration wherein the L-shaped enlarged head of the male members is substantially in register with the respective one of the L-shaped apertures.

7. The mandibular protrusion device of claim 1, wherein each one of the two lateral links is engageable with the mandibular dental tray by engaging a respective one of the flanges of the mandibular dental tray from an inner side towards an outer side thereof and wherein each one of the two lateral links is engageable with the maxillary dental tray by engaging the maxillary dental tray from the outer side towards an inner side of the wall.

8. The mandibular protrusion device of claim 1, wherein the elongated portions of the two lateral links have a curvature defined therein and each one of the two lateral links is thicker along sections of the elongated portion and towards the anterior end and the posterior end.

9. The mandibular protrusion device of claim 1, wherein the elongated portions of the two lateral links have a curvature defined therein and each one of the two lateral links is narrower in a central section of the elongated portion than close to the anterior end and the posterior end.

10. The mandibular protrusion device of claim 1, wherein the two lateral links are engaged with a respective one of the flanges of the mandibular dental tray above a contact plan defined between posterior sections of the maxillary dental tray and the mandibular dental tray and above an upper section of the wall of the mandibular dental tray.

11. The mandibular protrusion device of claim 1, wherein an anterior one of the male members protrude from the dental-tray facing face of the elongated portion of the two lateral links at the anterior end and a posterior one of the male members protrude from the flange-facing face of the elongated portion of the two lateral links at the posterior end and wherein the elongated portion of the two lateral links is protrusion free on the flange-facing face at the anterior end and is protrusion free on the dental-tray facing face at the posterior end.

12. The mandibular protrusion device of claim 1, wherein the male members protruding from or engageable with a respective one the lateral links protrude in opposed directions with respect to the dental-tray facing face and the flange-facing face of the respective one of the lateral links.

13. An intraoral orthosis having a right side and a left side, the intraoral orthosis comprising:
  a maxillary dental tray having a wall with an outer side, an anterior section, a left-side posterior section and a right-side posterior section, the wall defining a U-shaped dentition receiving cavity;
  a mandibular dental tray having a wall with an outer side, an anterior section, a left-side posterior section and a right-side posterior section, the wall defining a U-shaped dentition receiving cavity, the mandibular dental tray further comprising two flanges extending upwardly from a respective one of the posterior sections and outwardly from the outer side of the wall, wherein a lateral link receiving channel is defined between each one of the two flanges and the outer side of the wall of the mandibular dental tray; and
  two lateral links, each one of the lateral links having an elongated portion with an anterior end removably engageable with the maxillary dental tray, a posterior end opposed to the anterior end, a dental-tray facing face and a flange-facing face opposed to the dental-tray facing face, the posterior end being removably engageable with a respective one of the flanges of the mandibular dental tray, and located in a respective one of the lateral link receiving channels when engaged with the respective one of the flanges of the mandibular dental tray;
  wherein each one of the anterior section of the maxillary dental tray, the flanges of the mandibular dental tray, and the anterior ends and the posterior ends of the two lateral links comprises at least one of male members and female members to detachably engage the two lateral links with the mandibular dental tray and the maxillary dental tray at the posterior ends and the anterior ends, wherein the male members and the females members are complementary in shape and the male members protruding from or engageable with a respective one of the lateral links protrude in opposed directions with respect to the dental-tray facing face and the flange-facing face of the respective one of the lateral links; and wherein the complementary male and female members are engageable and disengageable from one another in at least one engagement/disengagement configuration that is not reached when the device is worn or in normal use, the at least one engagement/disengagement configuration being reached by rotating one of the maxillary dental tray and the mandibular dental tray in a configuration where the maxillary dental tray is located posteriorly of the flanges of the mandibular dental tray.

14. The intraoral orthosis of claim 13, wherein the at least one engagement/disengagement configuration is a single configuration for each one of the two lateral links.

15. The intraoral orthosis of claim 14, wherein the two lateral links comprise a right-side lateral link and a left-side lateral link, and wherein the engagement/disengagement configuration is different for the right-side lateral link and the left-side lateral link and an offset between the engagement/disengagement configurations of the two lateral links is greater than 30°.

16. The intraoral orthosis of claim 15, wherein the engagement/disengagement configuration for the right-side lateral link is reached by rotating one of the maxillary dental tray and the mandibular dental tray to a first angle and the engagement/disengagement configuration for the left-side lateral link is reached by rotating one of the maxillary dental tray and the mandibular dental tray to a second angle different from the first angle.

17. The intraoral orthosis of claim 13, wherein each one of the male members comprises a pivot portion rotatable into a corresponding one of the complementary female members when engaged together and connected to a substantially L-shaped enlarged head defined by two arms intersecting each other at an angle with the pivot portion being connected to the respective enlarged head at the intersection of the two arms; and each one of the female members comprises an L-shaped aperture; and wherein each one of the enlarged head is insertable into or disengageable from the respective one of the L-shaped apertures solely in the engagement/disengagement configuration wherein the L-shaped enlarged head is substantially in register with the respective one of the L-shaped apertures.

18. The intraoral orthosis of claim 13, wherein each one of the two lateral links is engageable with the mandibular dental tray by engaging a respective one of the flanges of the mandibular dental tray from an inner side towards an outer side thereof and wherein each one of the two lateral links is engageable with the maxillary dental tray by engaging the maxillary dental tray from the outer side towards an inner side of the wall.

19. The intraoral orthosis of claim 13, wherein the elongated portions of the two lateral links have a curvature defined therein and each one of the two lateral links is thicker along sections of the elongated portion and towards the anterior end and the posterior end.

20. The intraoral orthosis of claim 13, wherein the elongated portions of the two lateral links have a curvature defined therein and each one of the two lateral links is narrower in a central section of the elongated portion than close to the anterior end and the posterior end.

21. The intraoral orthosis of claim 13, wherein the two lateral links are engaged with a respective one of the flanges of the mandibular dental tray at least one of: above a contact plan between posterior sections of the maxillary dental tray and the mandibular dental tray and above an upper section of the wall of the mandibular dental tray.

22. The intraoral orthosis of claim 13, wherein the at least one engagement/disengagement configuration is reached when the anterior section of the maxillary dental tray is located rearwardly of the posterior sections of the mandibular dental tray.

23. The intraoral orthosis of claim 13, wherein an anterior one of the male members protrude from the dental-tray facing face of the elongated portion of the two lateral links at the anterior end and a posterior one of the male members protrude from the flange-facing face of the elongated portion of the two lateral links at the posterior end and wherein the elongated portion of the two lateral links is protrusion free on the flange-facing face at the anterior end and is protrusion free on the dental-tray facing face at the posterior end.

24. The intraoral orthosis of claim 13, wherein a first one and a second one of the male members provided on each one of the right side and the left side of the mandibular protrusion device protrude respectively towards and away from the outer side of the walls of the maxillary and mandibular dental trays when the lateral links are engaged therewith.

* * * * *